United States Patent
Kohl et al.

[11] Patent Number: 5,329,087
[45] Date of Patent: Jul. 12, 1994

[54] SYRINGE NEEDLE DESTRUCTION METHOD AND APPARATUS

[75] Inventors: Brad A. Kohl, 325 Skyline Pkwy., Athens, Ga. 30606; Douglas L. Armstrong, Atlanta; Byron L. Boylston, Woodstock; Keith G. Savas, Marietta; Mark G. Deveau, Stone Mountain; Scott Sadow, Woodstock, all of Ga.

[73] Assignee: Brad A. Kohl, Athens, Ga.

[21] Appl. No.: 72,901

[22] Filed: Jun. 7, 1993

[51] Int. Cl.5 .................. A61G 12/00; A61L 11/00; B23K 11/22
[52] U.S. Cl. .................. 219/68; 72/342.96
[58] Field of Search .......... 72/332, 334, 342.96; 219/68; 33/833, 707

[56] References Cited

U.S. PATENT DOCUMENTS

| | | | |
|---|---|---|---|
| 4,255,996 | 3/1981 | Choksi et al. | 83/140 |
| 4,445,644 | 5/1984 | Lemke | 241/99 |
| 4,628,169 | 12/1986 | Ch'ing-Lung | 219/68 |
| 4,860,958 | 8/1989 | Yerman | 241/23 |
| 4,877,934 | 10/1989 | Spinello | 219/68 |
| 4,905,916 | 3/1990 | Sorwick et al. | 241/23 |
| 4,961,541 | 10/1990 | Hashimoto | 219/68 |
| 4,965,426 | 10/1990 | Colombo | 219/68 |
| 4,969,379 | 11/1990 | Taylor et al. | 219/68 |
| 5,076,178 | 12/1991 | Kohl et al. | 219/68 |
| 5,166,488 | 11/1992 | Peppard | 219/68 |
| 5,282,428 | 2/1994 | Greville | 219/68 |
| 5,288,964 | 2/1994 | Walker | 219/68 |

FOREIGN PATENT DOCUMENTS 181866 7/1989 Japan ...................... 219/78

*Primary Examiner*—Daniel C. Crane
*Attorney, Agent, or Firm*—Kennedy & Kennedy

[57] ABSTRACT

A method and apparatus are disclosed for destroying syringe needles. The apparatus has an incinerator unit (16) into which a syringe needle may be inserted, crimped by a crimper (30), the needle measured between its tip and the sealing crimp, burned by passing an electric current corresponding to its measured length between the needle tip and the sealing crimp, and the burned needle severed by a cutting blade (36).

19 Claims, 5 Drawing Sheets

SYRINGE NEEDLE DESTRUCTION METHOD AND APPARATUS

TECHNICAL FIELD

This invention relates to methods and apparatuses for destroying syringe needles.

BACKGROUND OF THE INVENTION

Disposable hypodermic syringes are widely used in hospitals and other medical facilities to draw body fluids from and to inject medications into patients. These syringes are made disposable because of the difficulties and inefficiencies involved in re-sterilizing syringes for reuse. Because the syringes are intended to be disposed of after use, a problem arises as to their safe post-use storage and disposal and in preventing them from being recklessly reused by others. Indeed, in some countries laws prohibit syringes from being disposed of as ordinary waste since their sharp needle tips, as well as disease causing organisms sometimes carried by them, may injure hospital and waste disposal personnel.

To dispose of syringes safely, devices have been devised that mechanically sever the syringe needles from their barrels. These are exemplified by those shown in U.S. Pat. Nos. 4,255,996, 4,445,644 and 4,969,379. Though these devices do prevent reuse of syringes, a sharp needle stub remains intact and hazardous. Other types of syringe destruction devices grind the syringes into small pieces as shown in U.S. Pat. No. 4,905,916. These however do not provide for sanitary syringe residue disposal. Furthermore, their shearing action tends to release fluid contaminates to ambience.

Incinerators have also been used to destroy syringes is a sanitary manner. Bulk incineration of accumulated syringes however poses the threat of injury still occurring during accumulation and incineration input. Thus, portable devices have been used which can incinerate the needles by passing an electric current through them. This approach is described in U.S. Pat. No. 4,877,934 and 4,965,426. However, these devices leave the barrel portion of the syringe with an opening at one end through which contaminates may emerge to ambience. Furthermore, some pathogens contained within the needle and expelled from the syringe during insertion are not killed by the incineration process. Thus, another type of portable device has been devised which crimps the needle prior to passing an electric current through it to seal it. This type of device is shown in U.S. Pat. No. 5,076,178. A drawback of this device is that an electric current large enough to burn a long needle oftentimes causes a short needle to explode rather than burn. This explosion of the needle can allow pathogens within the needle to escape unharmed, often in an aerosol form. On the other hand, a current appropriate for a short needle may take too long a time to burn a long needle, if it does so at all.

It thus is seen that a need remains for a method and apparatus for destroying syringe needles in a more effective and efficient manner. It is to the provision of such that the present invention is primarily directed.

SUMMARY OF THE INVENTION

In a preferred form of the invention, a syringe needle destruction apparatus comprises a housing having an orifice through which a syringe needle may be inserted, a needle tip electric contact element mounted for movement along a needle path of travel within the housing in engagement with the needle tip between a position adjacent the orifice and a position distal from the orifice, and electric contact means mounted within the housing adjacent the orifice for establishing an electrical contact on the needle distally from the needle tip. The apparatus also has measuring means for measuring a displacement of the needle tip electric contact element along the needle path of travel from a position adjacent the orifice and a position distal from the orifice, means for establishing a voltage across the needle tip electric contact element and the electric contact means, and means for controlling the voltage established by the voltage establishing means as a function of needle tip electric contact element displacement measured by the measuring means.

In another preferred form of the invention, a method provides for destroying at least a portion of a needle that extends outwardly from the barrel and hub of a syringe to a needle tip. The method comprises the steps of inserting a portion of the needle into an incinerator while leaving the barrel outside of the incinerator, measuring the length of the portion of the needle inserted into the incinerator, and burning the needle by passing an electric current through the portion of the needle, the magnitude of the electric current being in relation to the measured length of the needle portion.

DETAILED DESCRIPTION

Figure 1:
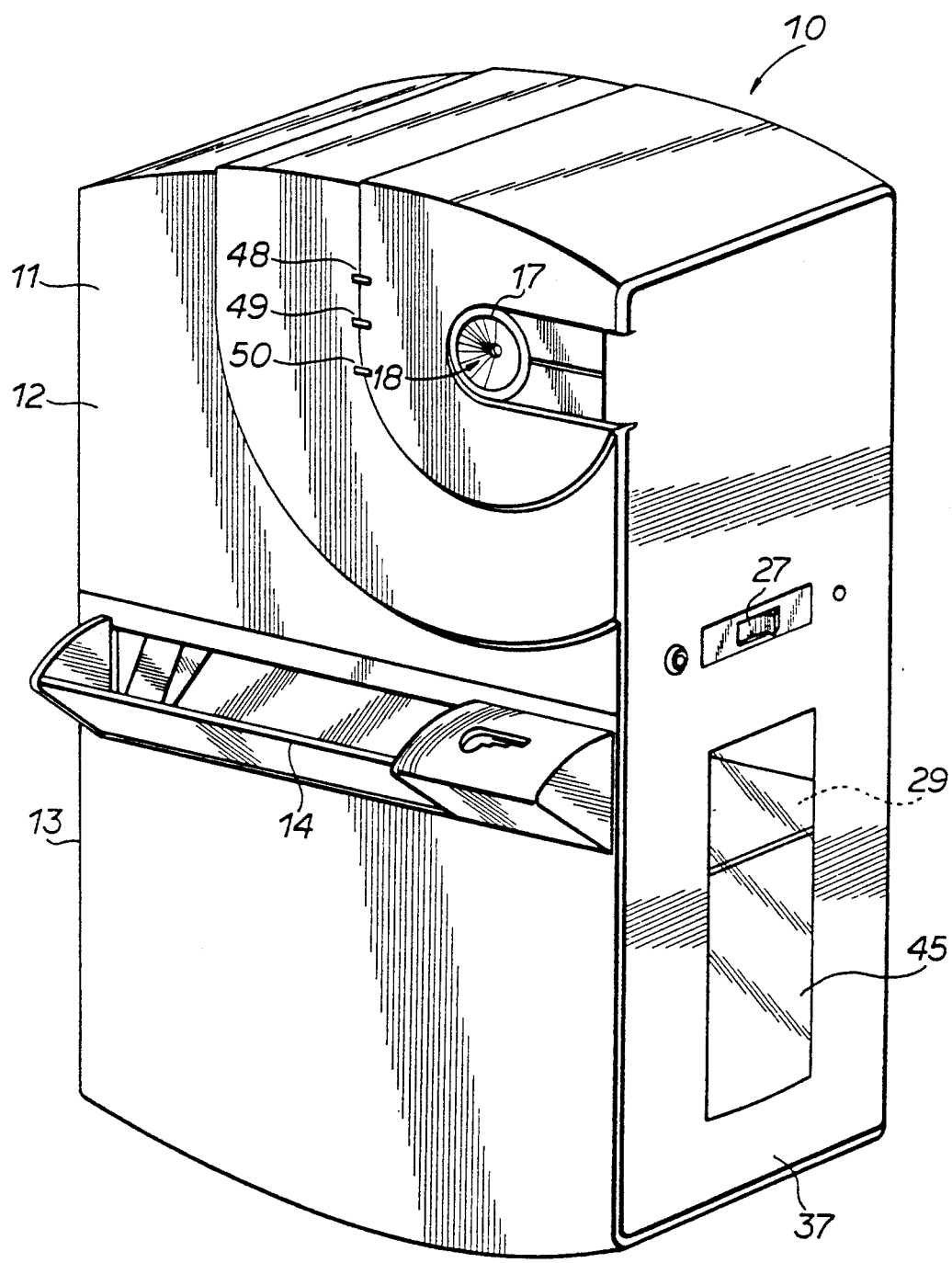
FIG. 1 is a perspective view of a syringe needle destruction apparatus that embodies principles of the invention is a preferred form.

With reference next to the drawings, there is shown an apparatus 10 having a housing 11. The apparatus has an upper working unit 12 for syringe needle destruction operations that extends from a lower, storage unit 13 in which residual syringe barrels may be collected and stored. The apparatus 10 has a pivotable side door 37 with a power switch 27 mounted thereon and a viewing window 45 therethrough. The storage unit 13 has a pivotable syringe disposal door 14 and a removable bin 29 located therein. The working unit 12 has a removable, incinerator unit 16 having a conically shaped needle receiving orifice guide 17 mounted about a central orifice 18.

Figure 2:
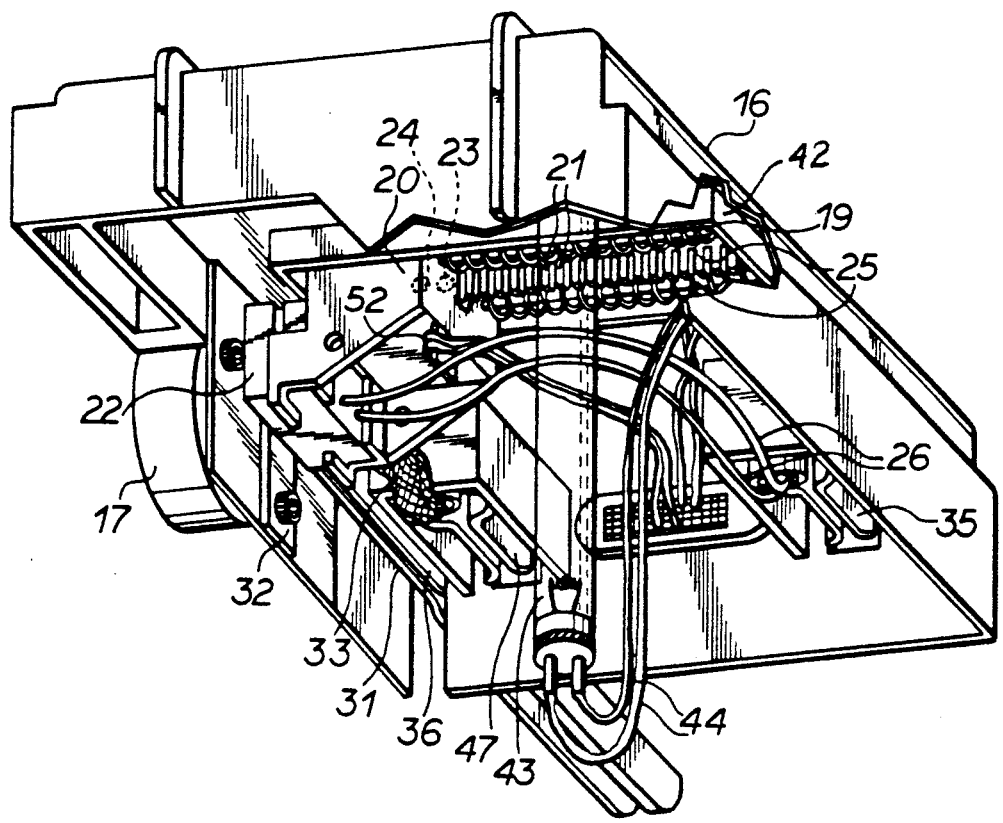
FIG. 2 is a perspective view of internal components of the apparatus of FIG. 1 shown with the housing removed for clarity of explanation and with its carriage in an initial position.

With reference next to FIG. 2, the incinerator unit 16 has guide means in the form of a pair of guide rods 19 mounted therein above the orifice guide 17. A spring biased carriage 20 is movably supported for travel upon the guide rods 19. The carriage 20 bears an electrode 22 with a face that faces and is aligned with the needle orifice 18. The incinerator unit 16 has measuring means in the form of an array of juxtaposed teeth 21 mounted therein between the guide rods 19 and a front photoelectric eye 23 and a rear photoelectric eye 24 mounted to the carriage 20. Eyes 23 and 24 are aligned so as to sense light passing between any two adjacent teeth 21. Coil springs 25 are mounted upon the guide rods with one of their ends abutting stop wall 42 and their opposite ends abutting the carriage so as to bias the carriage towards the needle orifice 18. Flexible conductors 26 connect the carriage electrode 23 to a transformer 28 through a quick disconnect coupler 35 with the carriage located in any position along the guide rods.

A needle crimping means 30 is mounted in incinerator unit 16 closely adjacent the needle orifice. The crimping means comprises an upper crimping plate 31 pivotably mounted on a pivot pin 34 above the orifice 18 and a stationary lower crimping plate 32 rigidly mounted below the needle orifice 18. The lower plate 32 also functions as an electrode and a conductor 33 electrically couples it with the transformer 28 through a quick disconnect coupler 47.

The apparatus also has means for severing needles that includes a pivotable cutting blade or shearing plate 36 pivotable mounted on a pivot pin 34 in sliding contact with the rear side of the upper crimping plate 31. Both the upper crimping plate 31 and the blade 36 extend through aligned openings in the wall of the incinerator unit 16 so that one of their end portions extends from the incinerator unit. An electric motor 40, mounted in the working unit 12, has its power output drive shaft coupled with both a crimping cam 38 and a cutting cam 39. The motor is electrically coupled to a controller 41, which is of conventional construction that preferably employs a microprocessor such as a 20 pin Motorola HC 6805 made by Motorola Inc. of Austin, Texas. An ultraviolet light 43 mounted in the incinerator unit 16 is also coupled with the controller 41 by a pair of conductors 44. A system ready LED type indicator lamp 48, a trouble/burn process LED type indicator lamp 49, and a full status LED type indicator lamp 50 are all mounted to the front of the working unit 12. Additionally, an unshown error code lamp is mounted within the lower unit 13 that is viewable through viewing window 45. Each of these lamps is electrically connected to the controller 41, while photoelectric eyes 23 and 24 are connected to the controller by conductors 52. The transformer 28 itself is coupled to the controller 41. An unshown high temperature sensor is mounted on the transformer 28 which is coupled with the controller.

An electromagnetic burn done switch 55 is mounted within the incinerator unit 16 so that the carriage 20 closes an electric circuit when it is positioned closely adjacent the orifice 18. An unshown motor home or cycle complete sensor is mounted adjacent the motor 40 to indicate that the cams have completed a full cycle and have returned to their initial, apparatus-ready positions prior to apparatus activation.

OPERATION

Figure 3A:
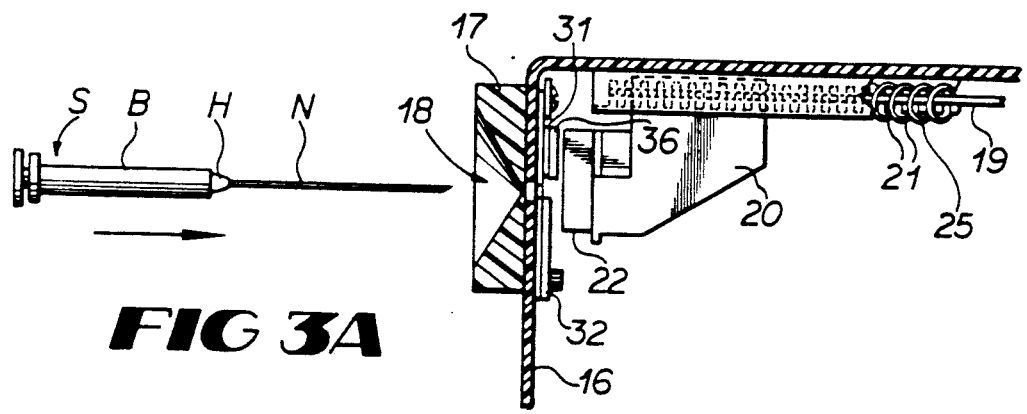
FIG. 3A–3F are a sequence of views, shown in cross-section, of a portion of the apparatus of FIG. 1, showing a syringe needle being inserted, crimped, incinerated and severed in accordance with a method of the invention.
Figure 3B:
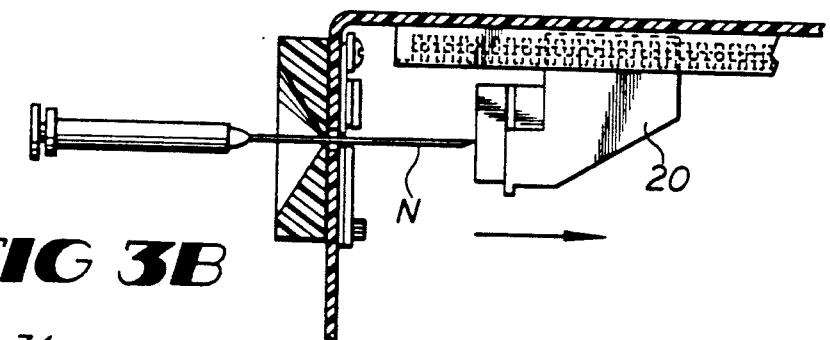
Figure 3C:
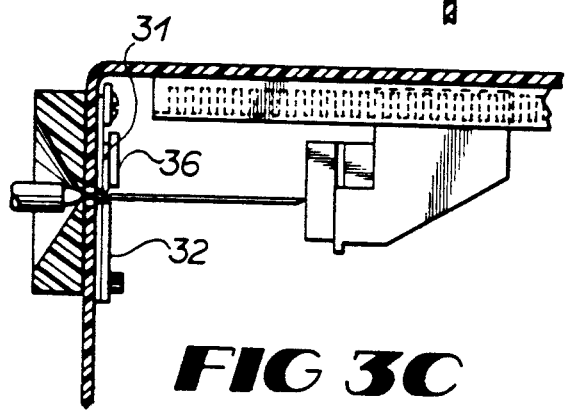

Operation of the apparatus may best by understood by reference to FIGS. 3A-3F and FIG. 4. With the power switch 27 positioned on, a conventional syringe S having a barrel B, a plastic needle hub H, and a metallic needle N is guided by an operator, such as a nurse, nurse's aid, or hospital attendant, into the needle receiving orifice 18, as shown in FIG. 3A. The conical shape of the orifice guide 17 serves to guide the needle tip into and through the orifice 18. As the needle N is pushed into the incinerator unit 16 it passes between the crimping plates 31 and 32 bringing its tip into contact with the carriage electrode 22. As the needle is pushed further into the unit it drives the carriage 20 away from the orifice 18 along guide rods 19, against the bias provided by spring 25, as shown in FIG. 3B. The carriage is moved in this manner until either the syringe hub H abuts the conical orifice guide 17, as shown in FIG. 3C, or until the carriage has traveled the maximum distance allowed by the guide rods 19 by engaging carriage stop wall 42. Carriage movement is limited to insure that an operator does not attempt to incinerate the entire length of an extraordinarily long needle in a single operations and thereby exceed power capacity limits. Such long needles are instead incinerated in a succession of operations as such operations are herein described.

As the carriage is driven away from the orifice 18 the front photoelectric eye 23 senses the light passing between the first and second tooth 21, the rear photoelectric eye 24 quickly thereafter also senses this light. This sensing sequencing of the sensors indicates to the controller that the carriage is moving forward, meaning away from orifice 18, and a reversing of this sensing sequence indicates a backwards movement of the carriage. The controller determines the length of the needle from the distance the carriage has moved from the orifice. This is done by calculating the number of teeth the eyes have traveled past in the forward direction. An increase in the determined length of the needle results in the controller increasing the power setting of the transformer, i.e. the magnitude of the electric current, to insure that needles of all lengths are provided with a current which properly burns them. For example, as a needle moves the carriage between its initial position adjacent orifice 18 and a distance $\frac{1}{4}$ inch therefrom, the controller sets the current at 25% of the maximum current of the transformer. As the carriage is driven further along the guide rails to a distance of between $\frac{1}{2}$ to 1 inch from its initial position the power level is set at 50%. From 1 to $1\frac{1}{2}$ inches from its initial position the power level is set to 75%, and from $1\frac{1}{2}$ inch to a maximum carriage distance of approximately 3 inches from its initial position the power level is set at 100%. The preferred transformer here is rated for 7 volts A.C. and for a maximum current of 40 amps as high current could cause sparking and welding of the needle to the electrodes.

Once the syringe needle N is fully inserted into the incinerator unit 16, as shown in FIG. 3C, a sensed momentary pause in carriage motion for a preselected time period is detected by the photoelectric eyes 23 and 24 which causes the controller to energize the motor 40 and the trouble/burn process lamp 49, and de-energize the system ready lamp 48. The motor then commences to rotate the crimping cam 38 and the cutting cam 39. The crimping cam 38 engages and pivots the upper crimping plate 31 about pivot pin 34 thereby crimping needle N between the upper crimping plate 31 and the lower crimping plate 32, as shown in FIG. 3C. The crimping of the needle serves the dual function of sealing the syringe needle residual stub and providing an electric contact with the needle at the crimp site since the lower plate 32 also functions as an electrode. With the needle crimp still held firmly by the plates 31 and 32, the controller next energizes the electrodes 23 and 32 by coupling them with the transformer 28 causing the selected current based on the length of the needle to flow through it causing the needle portion to burn and char.

Figure 3D:
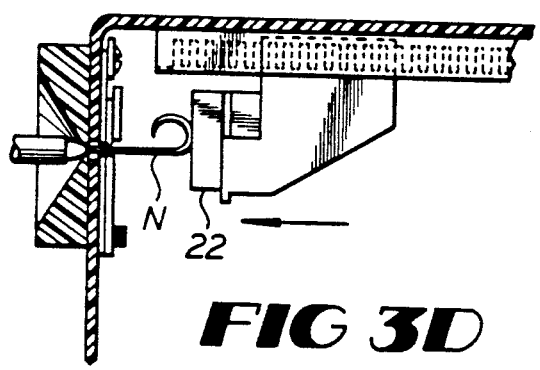

During the brief period of incineration, the spring 25 continuously urges electrode 22 towards electrode 32. This serves to maintain them in good contact with the needle and also to create a compaction force on the needle char to lengthen the time that the charring needle provides a conductive path between the electrodes. As incineration progresses and the needle weakens it becomes unable to hold the electrodes apart. As a result, the carriage and electrode 23 then advance towards the crimping means, as shown in FIG. 3D. This causes the needle to fold and twist which usually forms it into a compact, single extension needle residue char of a coil-like shape that usually remains attached to the unburned portion of the needle at its crimp. As the needle weakens and the carriage is advanced toward the crimping means the controller reduces the current passing through the needle in similar fashion to that previously described with reference to the position of the carriage with respect to the selected current level. The reduction of the current extends the useful life of the electrode, decreases power consumption, decreases the chances of sparking and welding of the needle to the electrodes, and decreases the chances of exploding the needle due to passing too large a current through the needle.

Figure 3E:
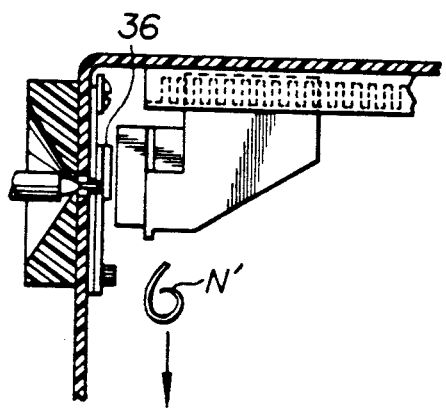
Figure 3F:
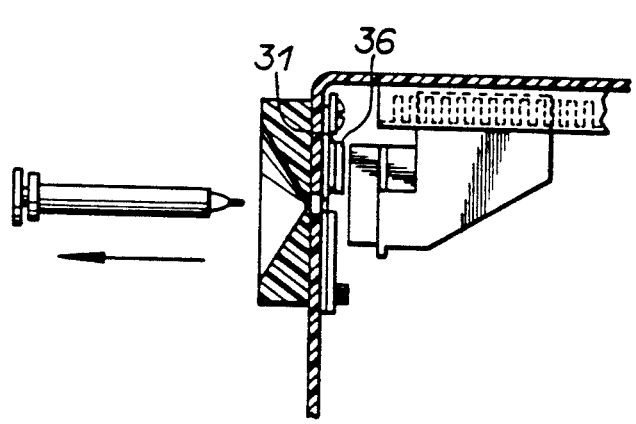
Figure 4:
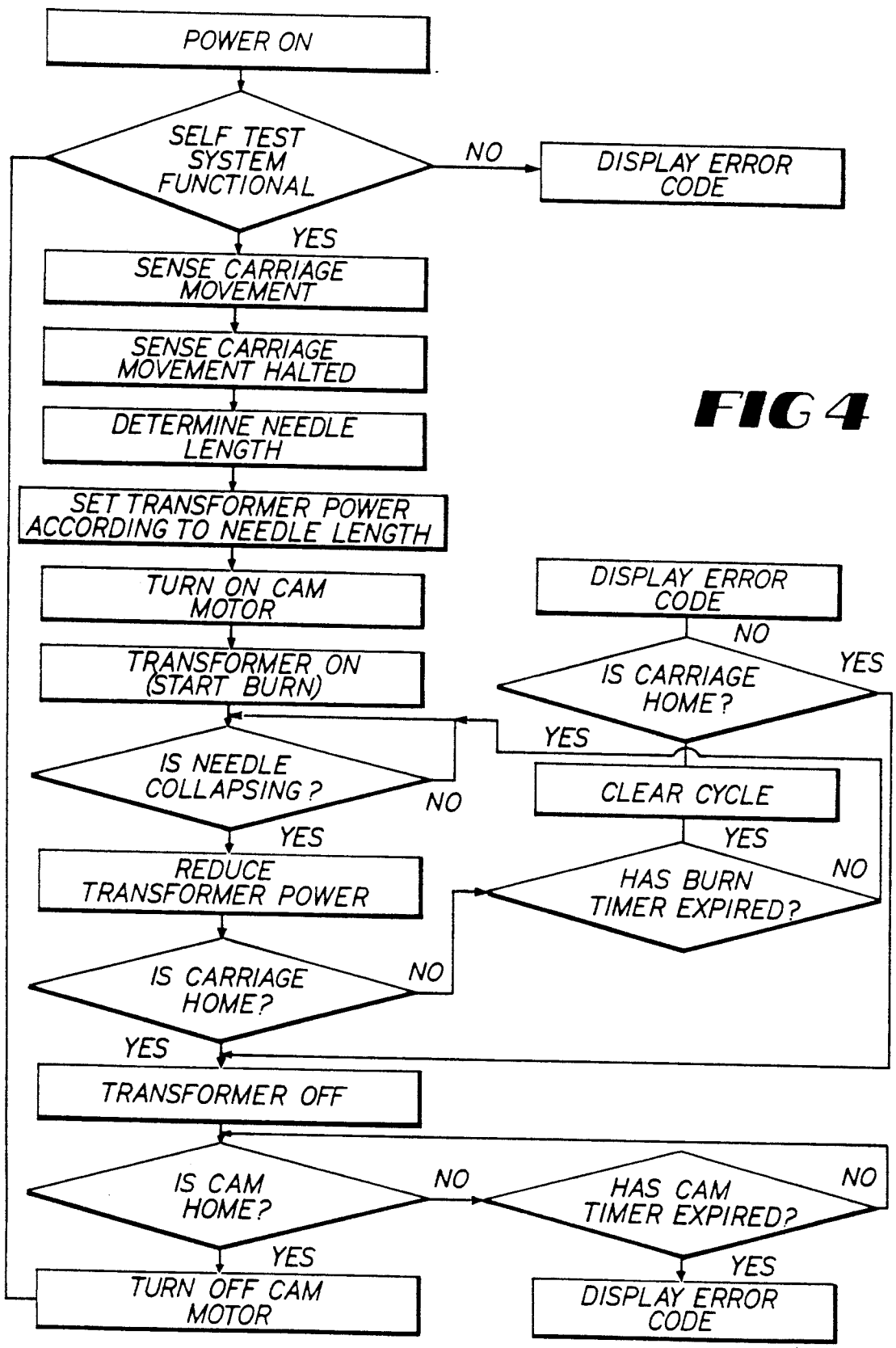
FIG. 4 is a flow diagram of the operation of the apparatus of FIG. 1 and method of the invention.
Figure 5:
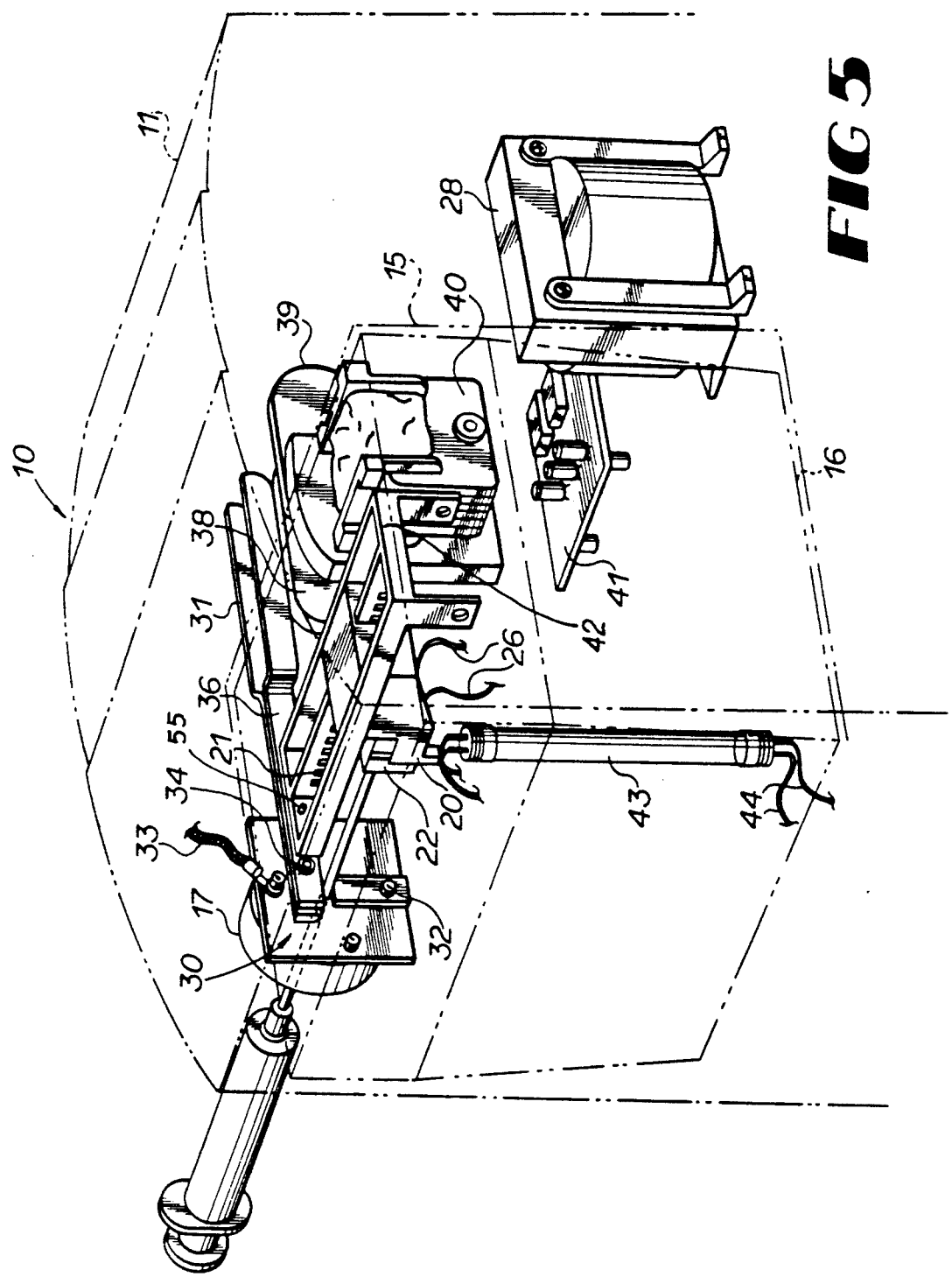
FIG. 5 is a perspective view of internal components of the apparatus of FIG. 1 shown with the housing and a portion of the electric wiring removed for clarity and with its carriage in an advanced position.

As the returning carriage nears its initial position adjacent the crimping means 30, the carriage closes the electromagnetic burn done switch thus indicating to the controller that the burn process is complete. The controller then de-energizes the electrodes just prior to the carriage returning to its initial position. This prevents an arcing between the electrodes and a welding of the needle to the electrodes. If the burn done switch has not been interrupted after expiration of a preselected time period, such as two seconds from the time of burn initiation, the controller de-energizing the motor 40 to allow the needle to burn for an additional 2 second time period and then re-energizes the motor and de-energizes the electrodes. The cutting cam 39 is now rotated to a position forcing the cutting blade 36 downward through the needle char closely adjacent the crimp. The cutting blade severs the residue char N' whereupon it free falls, as shown in FIG. 3E, to the bottom of the incinerator. Finally, as shown in FIG. 3F, with the crimping plates once again separated the needle crimp is released enabling the operator to remove the syringe and its short, sealed, needle stub from the incinerator unit 16 and place it in the lower storage unit 13.

Should the electromagnetic switch 55 indicate that the carriage has not returned to its initial position after a burn cycle, the controller will attempt to clear the fault by energizing motor 40 to initiate 3 cycles of the crimping plate and cutting blade 36. If the carriage has still not returned the controller causes the display of an error code on the error code lamp and prevents the initiating of another burn cycle.

Once the cams have fully returned to their initial positions the motor home sensor inputs a signal to the controller 41 which de-energizes the motor 40, re-energizes the system ready lamp 48, and de-energizes the trouble/burn process 49 to indicate that the apparatus is reset and ready to incinerate another needle.

Though most pathogens within the needle are killed by their incineration, some heat resistant ones may not be. Also, some pathogens may be expelled during insertion and operation of the needle into the apparatus. For these reasons the incinerator is also provided with a germicidal ultraviolet light 43 which is energized by the controller for a short time following needle severance to kill such remaining pathogens.

Finally, the controller also counts the number of burn cycles completed so that after a preselected number of cycles the controller will flash the full status lamp 50 for a 72 hour grace period. If the incinerator unit 16 is not replaced within this grace period the full status lamp is continuously illuminated and the controller will not initiate another burn cycle.

From the foregoing, it is seen that a method and apparatus for destroying syringe needles is now provided which overcomes problems associated with those of the prior art. It should however be understood that the just described embodiment merely illustrates principles of the invention in a preferred form. Many modifications, additions and deletions may, of course, be made thereto without departure from the spirit and scope of the invention as set forth in the following claims.

We claim:

1. A syringe needle destruction apparatus comprising a housing having an orifice through which a syringe needle may be inserted, a needle tip electric contact element mounted for movement along a needle path of travel within said housing in engagement with the needle tip between a position adjacent said orifice and a position distal from said orifice, electric contact means mounted within said housing adjacent said orifice for establishing an electrical contact on the needle distally from the needle tip, measuring means for measuring a displacement of said needle tip electric contact element along the needle path of travel from a position adjacent said orifice and a position distal from said orifice, means for establishing a voltage across said needle tip electric contact element and said electric contact means, and means for controlling and varying the voltage established by said voltage establishing means as a function of needle tip electric contact element displacement measured by said measuring means.

2. The syringe needle destruction apparatus of claim 1 wherein said needle tip electric contact element is mounted for movement by mounting means that comprises at least one guide rod mounted within said housing extending substantially parallel to the needle path of travel, and a carriage movably mounted upon said rod and spring biased towards said orifice.

3. The syringe needle destruction apparatus of claim 1 wherein said measuring means comprises an array of juxtaposed teeth mounted within said housing and extending substantially parallel to the needle path of travel and means for counting the number of teeth passed as said carriage is moved along the needle path of travel.

4. The syringe needle destruction apparatus of claim 1 further comprising crimping means mounted within said housing adjacent said orifice for crimping a syringe needle to substantially seal the syringe.

5. The syringe needle destruction apparatus of claim 4 wherein said crimping means comprises a pair of plates and motor means coupled to at least one of said plates for imparting relative movement of the crimping plates towards each other.

6. The syringe needle destruction apparatus of claim 1 further comprising cutting means mounted within said housing proximal said orifice for severing a burned portion of a needle from a substantially unburned portion.

7. The syringe needle destruction apparatus of claim 6 further comprising crimping means mounted within said housing adjacent said orifice for crimping a syringe needle to substantially seal the syringe.

8. A syringe needle destruction apparatus comprising:
   means for receiving and containing a needle portion of a syringe;
   means for measuring the length of the needle portion;
   means for establishing a voltage across said needle portion; and
   means for controlling and varying said means for establishing a voltage as a function of needle length measured by said measuring means.

9. The syringe needle destruction apparatus of claim 8 further comprising severing means for severing at least a portion of a needle.

10. The syringe needle destruction apparatus of claim 8 further comprising crimping means for forming a crimp in the needle portion distally from a needle tip in contact with said voltage establishing means.

11. The syringe needle destruction apparatus of claim 10 further comprising severing means for severing the needle portion adjacent the crimp.

12. The syringe needle destruction apparatus of claim 9 further comprising crimping means for forming a crimp in the needle portion distally from the needle tip in contact with said voltage establishing means.

13. The syringe needle destruction apparatus of claim 8 wherein said means for measuring the length of the needle portion comprises guide means mounted within said housing extending substantially parallel to the needle path of travel, a carriage movably mounted upon said guide means, an array of juxtaposed teeth mounted adjacent said carriage substantially parallel to the needle path of travel and means for detecting and counting the number of teeth passing past said carriage as said carriage moves along said track.

14. The syringe needle destruction apparatus of claim 13 wherein said means for establishing a voltage comprises a needle tip contact element mounted to said carriage for contact with a tip of the needle and a contact element mounted to said receiving means adjacent said carriage for contact with the needle portion distally from the needle tip.

15. A method of destroying at least a portion of a needle that extends outwardly from the barrel and hub of a syringe to a needle tip, and with the method comprising the steps of:
   (a) inserting a portion of the needle into an incinerator while leaving the barrel outside of the incinerator;
   (b) measuring the length of the inserted portion of the needle within the incinerator; and
   (c) burning the needle by passing an electric current through the portion of the needle, the magnitude of the electric current being in relation to the measured length of the needle portion.

16. The method of claim 15 further comprising the step of:
   (d) forming a sealing crimp in the needle adjacent the syringe hub.

17. The method of claim 16 further comprising the step of:
   (e) severing the burned portion of the needle adjacent the crimp.

18. The method of claim 15 further comprising the step of:
   (d) severing the burned portion of the needle.

19. The method of claim 15 wherein step (c) the magnitude of the electric current is reduced as the needle is burned.

* * * * *